US006780615B1

(12) United States Patent
Duan (10) Patent No.: US 6,780,615 B1
(45) Date of Patent: Aug. 24, 2004

(54) PRODUCTION OF RECOMBINANT MONELLIN USING METHYLOTROPHIC YEAST EXPRESSION SYSTEM

(75) Inventor: Lingxun Duan, San Diego, CA (US)

(73) Assignee: Genway Biotech Inc., San Diego, CA (US)

( * ) Notice: Subject to any disclaimer, the term of this patent is extended or adjusted under 35 U.S.C. 154(b) by 0 days.

(21) Appl. No.: 09/869,445

(22) PCT Filed: Dec. 9, 1999

(86) PCT No.: PCT/US99/29213

§ 371 (c)(1),
(2), (4) Date: Jun. 26, 2001

(87) PCT Pub. No.: WO00/40603

PCT Pub. Date: Jul. 13, 2000

Related U.S. Application Data (60) Provisional application No. 60/114,529, filed on Dec. 31, 1998.

(51) Int. Cl.[7] .................................................. C12P 21/04
(52) U.S. Cl. .................. 435/69.7; 435/70.1; 435/254.1; 536/23.4; 536/23.1; 530/350
(58) Field of Search ............................. 536/23.4, 23.1; 435/254, 69.7, 70.1, 69.1, 69.9, 74; 530/350, 395

(56) References Cited

U.S. PATENT DOCUMENTS

| | | | |
|---|---|---|---|
| 3,878,184 A | 4/1975 | Dobry | |
| 3,998,798 A | 12/1976 | Cagan et al. | |
| 4,300,576 A | 11/1981 | van der Loo et al. | |
| 4,412,984 A | 11/1983 | van der Loo et al. | |
| 4,562,076 A | 12/1985 | Arnold et al. | |
| 4,837,148 A | 6/1989 | Cregg | |
| 4,855,231 A | 8/1989 | Stroman et al. | |
| 4,882,279 A | 11/1989 | Cregg | |
| 4,929,555 A | 5/1990 | Cregg et al. | |
| 5,122,465 A | 6/1992 | Cregg et al. | |
| 5,234,834 A | 8/1993 | Fischer et al. | |
| 5,264,558 A | 11/1993 | Kim et al. | |
| 5,324,639 A * | 6/1994 | Brierley et al. ............ | 435/69.4 |
| 5,478,923 A * | 12/1995 | Kim et al. .................. | 530/300 |
| 5,487,983 A | 1/1996 | Kim et al. | |
| 5,670,339 A | 9/1997 | Kim et al. | |
| 5,672,372 A | 9/1997 | Kim et al. | |
| 6,300,099 B1 * | 10/2001 | Sledziewski et al. ...... | 435/69.1 |

FOREIGN PATENT DOCUMENTS

| | | |
|---|---|---|
| EP | 0821055 | 12/2003 |
| WO | WO 88/10265 | 12/1988 |

OTHER PUBLICATIONS

Abdulaev et al., Protein Expression and Purification (1997) 10:61–69.
Bohak and Li, Biochimica et Biophysica Acta (1976) 427:153–170.
Cagan, Science (1973) 181:32–35.
Cregg et al., Bio/Technology (1993) 11:905–910.
Dansby, Nature Biotechnology (1997) 15:419–420.
Ferrarese et al., FEBS Letters (1998) 422:23–26.
Ferrari et al., FEBS Letters (1997) 401:73–77.
Fidler et al., Journal of Molecular Endocrinology (1998) 21:327–336.
Fierobe et al., Protein Expression and Purification (1997) 9:159–170.
Frank and Zuber, HoppeSeyler's Z. Physiol. Chem. (1976) 357:585–592.
Heim et al., Biochimica et Biophysica Acta (1998) 1396:306–319.
Hudson and Biemann, Biochemical and Biophysical Research Communications (1976) 71(1):212–220.
International Search Report mailed on Jul. 6, 2000, for PCT patent application No. PCT/US99/29213 filed on Dec. 9, 1999, 4 pages.
Jönsson et al., Curr. Genet. (1997) 32:425–430.
Kim et al., Protein Engineering (1989) 2(8):571–575.
Kondo et al., Nature Biotechnology (1997) 15:453–457.
Kotake et al., Journal of Lipid Research (1996) 37:599–605.
Martinez–Ruiz et al., Protein Expression and Purification (1998) 12:315–322.
Merkle et al., Biochimica et Biophysica Acta (1997) 1336:132–146.
Morris and Cagan, Biochimica et Biophysica Acta (1972) 261:114–122.
Morris et al., Journal of Biological Chemistry (1973) 248(2):534–539.
Paifer et al., Yeast (1994) 10:1415–1419.
Ogata et al., Nature (1987) 328:739–742.
Ohi et al., Yeast (1996) 12(1):31–40.
Skory et al., Curr. Genet. (1996) 30:417–422.
Sadhukhan et al., Journal of Biological Chemistry (1996) 271(31):18310–18313.
Tsujikawa et al., Yeast (1996) 12:541–553.
van der Wel and Loeve, FEBS Letters (1973) 29(2):181–184.
Vedvick, Current Opinion in Biotechnology (1991) 2:742–745.
Vollmer et al., Journal of Immunological Methods (1996) 199:47–54.
Wuebbens et al., Biochemistry (1997) 36:4327–4336.
Zhu et al., Archives of Biochemistry and Biophysics (1998) 352(1):1–8.

* cited by examiner

*Primary Examiner*—James Ketter
*Assistant Examiner*—Konstantina Katcheves
(74) *Attorney, Agent, or Firm*—Morrison & Foerster LLP (57) ABSTRACT

The present invention relates to a single-chain monellin-like protein which is stable and which is at least 100-fold sweet as compared to sucrose on the weight basis. The present invention also relates to a nucleic acid encoding said monellin-like protein. Preferably, the nucleic acid further comprises a promoter and a signal sequence for directing expression and secretion of the encoded monellin-like protein in the methylothrophic yeast *Pichia pastoris*. The present invention further relates to a recombinant *Pichia pastoris* cell containing the nucleic acid encoding the monellin-like protein, a process for producing the monellin-like protein from the recombinant *Pichia pastoris* and product of the process.

33 Claims, 8 Drawing Sheets

```
GGT GAG TGG GAG ATT ATT GAC ATT GGT CCA TTC ACT
Gly Gly Trp Glu Ile Ile Asp Ile Gly Pro Phe Thr

CAA AAC TTG GGT AAG TTC GCT GTT GAC GAG GAG AAC
Gln Asn Leu Gly Lys Phe Ala Val Asp Glu Glu Asn

AAG ATT GGT CAA TAC GGT AGA TTG ACT TTC AAC AAG
Lys Ile Gly Gln Tyr Gly Arg Leu Thr Phe Asn Lys

GTT ATT AGA CCA TGT ATG AAG AAG ACT ATT TAC GAG
Val Ile Arg Pro Cys Met Lys Lys Thr Ile Tyr Glu

AAC GAG GGT TCT AGA GAG ATT AAG GGT TAC GAG TAC
Asn Glu Gly Ser Arg Glu Ile Lys Gly Tyr Glu Tyr

CAA TTG TAC GTT TAC GCT TCT GAC AAG TTG TTC CGT
Gln Leu Tyr Val Tyr Ala Ser Asp Lys Leu Phe Arg

GCT GAC ATT TCT GAG GAC TAC AAG ACT CGT GGT CGT
Ala Asp Ile Ser Glu Asp Tyr Lys Thr Arg Gly Arg

AAG TTG TTG AGA TTC AAC GGT CCA GTT CCA CCA CCA
Lys Leu Leu Arg Phe Asn Gly Pro Val Pro Pro Pro

TAA
Stop
```

5' AGA ATT CGG TGA GTG GGA GAT TAT TGA CAT TGG TCC ATT CAC TCA AAA CTT GG 3'

M2

5' GAA CAA GAT TGG TCA ATA CGG TAG ATT GAC TTT CAA CAA GTT TAT TAG GCC ATG T 3'

M3

5' GAG ACC GAG GGT TCT AGA GAG ATT AAG GGT TAC GAG TAC CAA TTG TAC GTT TAC GCT TC 3'

M4

5' GTG CTG ACA TTC CTG AGG ACT ACA AGA CTC GTG GTC GTA AGT TGT TGA GAT TC 3'

N1

5' GTA TTG ACC AAT CTT GTT CTC CTC GTC AAC AGC GAA CTT ACC CAA GTT TTG AGT GAA TG 3'

N2

5' CTC TAG AAC CCT CGT TCT CGT AAA TAG TCT TCT TCA TAC ATG GTC TAA TAA CCT TG 3'

N3

5' GTC CTC AGA AAT GTC AGC ACG GAA CAA CTT GTC AGA AGC GTA AAC GTA CAA TTG

N4

5' AGA ATT CTT ATG GTG GTG GAA CTG GAC CGT TGA ATC TCA ACA ACT TAC GAC 3'

Comments for pGWYS1 (3479 bp)

GAP Promoter region: 1-483
Alpha-factor signal sequence: 493-760
Monellin coding region: 762-1059
3' AOX 1 termination region: 1060-1306
TEF1 Promoter region: 1307-1709
EM7 Promoter region: 1710-1781
Sh ble ORF: 1782-2518
CYC1 termination region: 2159 2477
ColE1 origin ( pUC-derived): 2478-3479

Lane 1. Protein MW Marker

Lane 2. 5ul Culture Medium

Lane 3. Partially Purified Recombinant Single Chain Monellin

Lane 4. 40ug Native Monellin

PRODUCTION OF RECOMBINANT MONELLIN USING METHYLOTROPHIC YEAST EXPRESSION SYSTEM

This application claims the benefit of priority under 35 U.S.C. §119(e) to U.S. provisional application Serial No. 60/114,529 to Lingxun Duan, filed Dec. 31, 1998, and entitled PRODUCTION OF RECOMBINANT MONELLIN USING METHYLOTROPHIC YEAST EXPRESSION SYSTEM.

1. FIELD OF THE INVENTION

The present invention relates to a single-chain monellin-like protein which is stable and which is at least 100-fold sweet as compared to sucrose on the weight basis. The present invention also relates to a nucleic acid encoding said monellin-like protein. Preferably, the nucleic acid further comprises a promoter and a signal sequence for directing expression and secretion of the encoded monellin-like protein in the methylotrophic yeast *Pichia pastoris*. The present invention further relates to a recombinant *Pichia pastoris* cell containing the nucleic acid encoding the monellin-like protein, a process for producing the monellin-like protein from the recombinant *Pichia pastoris* and product of the process.

2. BACKGROUND ART

2.1. Monellin

Monellin belongs to a family of intensely sweet proteins derived from tropical plants (Dansby, *Nature Biotechnology*, 1997, 15:419–420). Monellin is about 3,000-fold sweet as compared to sucrose. Other similar proteins include thaumatin, miraculin, mabinlin, pentadin and aspartame (Id.) Monellin was first isolated from the West African Plant *Dioscoreophyllum comminisii* (U.S. Pat. Nos. 3,878,184 and 3,998,798; Morris and Cagan, *Biochim. Biophys. Acta*, 1972, 261:114–122). The amino acid sequence, the three-dimensional structure and various physical and chemical properties of monellin have been characterized (Ogata, et al., *Nature*, 1987, 328:739–742; Morris et al., *J. Biol. Chem.*, 1973, 248:534–539; Cagan, *Science*, 1973, 181:32–35; Bohak and Li, *Biochim. Biophys. Acta*, 1976, 427:153–170; Hudson and Beeman, *Biochem. Biophys. Res. Comm.*, 1976, 71:212–220; Van der Wel and Loeve, *FEBS Lett.*, 1973, 29:181–183; and Frank and Zuber, *HoppeSeyler's Z Physiol. Chem.*, 1976, 357:585–592).

U.S. Pat. No. 4,300,576 discloses smoking articles containing thaumatin or monellin. U.S. Pat. No. 4,562,076 discloses chewing gum with coating of thaumatin or monellin. U.S. Pat. No. 4,412,984 discloses flavor potentiated oral compositions containing thaumatin or monellin. However, despite its potential as low-calorie sweeteners, wide commercial application of monellin is hampered by concerns over its poor stability to heat and pH, lack of access to sources of supply of the plant and uncertainty in the regulatory climate for food additives (Dansby, *Nature Biotechnology*, 1997, 15:419–420).

In 1989, Sung-Hou Kim's group reported production of single-chain monellin in *E. coli* by genetic engineering (Kim et al., *Protein Eng.*, 1989, 2:571–575). The purified single-chain monellin was found to be more heat-stable and tolerant to a wide pH range, but retained the intensity of sweetness. Several aspects of this invention have been the subject of certain U.S. patents. For example, U.S. Pat. No. 5,234,834 discloses constructs for expression of single-chain monellin in plant cells. U.S. Pat. No. 5,487,923 discloses a sweet proteinaceous compound of the formula B-C-A, wherein B represents a peptide portion at least 90% homologous to residues 1–46 of the B chain of native monellin and modified only by conservative substitutions; C is a covalent bond or is a hydrophilic, physiologically acceptable covalent linker capable of providing a spacing length equivalent to a peptide of 1–10 amino acids selected so as to reside on the external portion of the molecule and not to disturb the native conformation; and A represents a peptide at least 90% homologous to residues 6–45 of the A chain of native monellin and modified only by conservative substitution. U.S. Pat. No. 5,487,983 discloses an expression system for making the single-chain monellin disclosed in U.S. Pat. No. 5,487,923. U.S. Pat. No. 5,670,339 discloses DNA encoding the single-chain monellin disclosed in U.S. Pat. No. 5,487,923. U.S. Pat. No. 5,672,372 discloses methods for sweetening a food composition with the single-chain monellin disclosed in U.S. Pat. No. 5,487,923. U.S. Pat. No. 5,264,558 discloses a single-chain monellin protein that is, in a standard taste test, at least 50 times that of sucrose on a weight basis.

Recently, Kondo et al., *Nature Biotechnology*, 1997, 15:453–457 discloses heterologous expression of a single-chain monellin protein in the yeast *Candida utilis* intracellularly. It reports that monellin was produced at a high level, accounting for >50% of the soluble protein.

2.2. Expression of Heterologous Proteins in *Pichia Pastoris*

The methylotrophic yeast *Pichia pastoris* has been used as a protein expression system. Several aspects of this expression system have been the subject of certain U.S. patents. For example, U.S. Pat. No. 4,837,148 discloses autonomous replication sequences for *Pichia pastoris*. U.S. Pat. No. 4,855,231 discloses regulatory region for heterologous gene expression in *Pichia pastoris* cells. U.S. Pat. No. 4,882,279 discloses site selective genomic modification of *Pichia pastoris*. U.S. Pat. No. 4,929,555 discloses a method for making whole cells of *Pichia pastoris* competent for transformation. U.S. Pat. No. 5,122,465 discloses a process for generating a selectable phenotype in strains of *Pichia pastoris*. U.S. Pat. No. 5,324,639 discloses production of insulin-like growth factor-1 in methylotrophic cells, including *Pichia pastoris* cells.

A number of signal sequences have been used to direct secretion of heterologous proteins expressed in *Pichia pastoris* cells. Examples of such signal sequences include, but are not limited to, the signal sequence of *Pichia pastoris* acid phosphatase, the signal sequence of *Aspergillus giganteus* alpha-Sarcin (Martinez-Ruiz et al., *Protein Expr. Purif.*, 1998, 12(3):315–22; Abdulaev et al., *Protein Expr. Purif.*, 1997, 10(1):61–9; Kotake et al., *J. Lipid Res.*, 1996, 37(3): 599–605), the signal sequence of alpha-N-Acetylgalactosaminidase (alphaNAGAL, EC 3.2.1.49) (Zhu et al., *Arch. Biochem, Biophys.*, 1998, 352(1):1–8), the signal peptide of the OmpA protein (Heim et al., *Biochim. Biophys. Acta.*, 1998, 1396(3):306–19), the signal sequence of the mouse alpha-factor signal (cCell) or the native signal sequence of pepper endo-beta-1,4-glucanases (Ferrarese et al., *FEBS Lett.*, 1998, 422(1):23–6), signal peptide of laccase isolated from the ligninolytic fungus Trametes (Jonsson et al., *Curr. Genet.*, 1997, 32(6):425–30), signal peptide of murine lysosomal acid alpha-mannosidase (Merkle et al., *Biochim. Biophys. Acta.*, 1997, 1336(2):132–46), signal peptide of the porcine inhibitor of carbonic anhydrase (Wuebbens et al., *Biochemistry*, 1997, 36(14):4327–36), signal sequence of *Aspergillus awamori* glucoamylase (Fierobe et al., *Protein Expr. Purif.*, 1997, 9(2):159–70), signal sequence of mouse major urinary protein (Ferrari et al., *FEBS Lett.*, 1997, 401(1):73–7), signal sequence of pho1 (Skory et al., *Curr. Genet.*, 1996, 30(5):417–22), signal sequence of rabbit angiotensin-converting enzyme (ACE) (Sadhukhan et al., *J. Biol. Chem.*, 1996, 271(31):18310–3), prepeptide sequence of *Pichia pastoris* aspartic proteinase (Tsujikawa et al., *Yeast*, 1996, 12(6):541–53), signal sequence of *Pichia pastoris* PRC1 (Ohi et al., *Yeast*, 1996, 12(1):31–40), the signal sequence of a bacterial thermostable alpha amylase and SUC2 gene signal sequence from *Saccharomyces cerevisiae* (Paifer et al., *Yeast*, 1994, 10(11): 1415–9) and the signal sequence of *Saccharomyces cerevisiae* mating pheromone α-factor (Fidler et al., *J. Mol. Endocrinol.*, 1998, 21(3):327–336).

Although the methylotrophic yeast *Pichia pastoris* has been used successfully for the production of various heterologous proteins, U.S. Pat. No. 5,324,639 discloses that at the present level of understanding of methylotrophic yeast expression systems, it is unpredictable whether a given gene can be expressed to an appreciable level in such yeast or whether the yeast host will tolerate the presence of the recombinant gene product in its cells. U.S. Pat. No. 5,324,639 further discloses that it is especially difficult to foresee if a particular protein will be secreted by the methylotrophic yeast host, and if it is, at what efficiency. For example, Vollmer et al., *J. Immunol. Methods*, 1996, 199(1):47–54, reports that when the 323 amino acid residues of the human sIL-6R are inserted into an expression/secretion vector suitable for the methylotrophic yeast *Pichia pastoris*, no detectable expression and secretion of the recombinant protein was obtained. Up to date, monellin has not been expressed and secreted using the *Pichia pastoris* expression system.

Given the great interest in the commercial application of monellin, there is a great need for a more efficient method for producing stable monellin which still retains its native sweet intensity and which simplify down stream purification procedures. The present invention addresses these and other needs in the art. Citation of references hereinabove shall not be construed as an admission that such references are prior art to the present invention.

3. SUMMARY OF THE INVENTION

The present invention relates to an isolated nucleic acid comprising a nucleotide sequence encoding a chimeric protein, said chimeric protein comprises, from N-terminus to C-terminus: a) a first peptidyl fragment consisting of an amino acid sequence that has at least 40% identity to residues 1–50 of the B chain of native monellin, in which the percentage identity is determined over an amino acid sequence of identical size to the B chain of native monellin; b) a peptidyl bond, or a second peptidyl fragment consisting of 1–12 amino acids; and c) a third peptidyl fragment consisting of an amino acid sequence that has at least 40% identity to residues 1–45 of the A chain of native monellin, in which the percentage identity is determined over an amino acid sequence of identical size to the A chain of native monellin, wherein said chimeric protein is stable and a given amount of said chimeric protein is at least 100-fold sweet as compared to the identical amount of sucrose, and within said nucleic acid, codons which are preferably used by yeast cells are used. Preferably, the isolated nucleic acid further encodes a promoter which is capable of directing protein expression in *Pichia pastoris* and/or an amino acid sequence which is capable of directing secretion of the encoded chimeric protein from *Pichia pastoris*.

The present invention also relates to a recombinant *Pichia pastoris* cell containing the above nucleic acids. The present invention further relates to a process for producing a chimeric protein comprising growing a recombinant *Pichia pastoris* cell containing the above nucleic acid such that the encoded chimeric protein is expressed and secreted by the cell, and recovering the expressed and secreted chimeric protein. Finally, the present invention relates to products of the above processes.

5. DETAILED DESCRIPTION OF THE INVENTION

The present invention provides a nucleic acid encoding a single-chain monellin-like protein which is stable and which is at least 100-fold sweet as compared to sucrose on the weight basis. Preferably, the nucleic acid further comprises a promoter and a signal sequence for directing expression and secretion of the encoded monellin-like protein in the methylotrophic yeast *Pichia pastoris*. The present invention also provides a recombinant *Pichia pastoris* cell containing the nucleic acid encoding the monellin-like protein, a process for producing the monellin-like protein from the recombinant *Pichia pastoris* and product of the process.

For clarity of disclosure, and not by way of limitation, the detailed description of the invention is divided into the subsections which follow.

5.1. Nucleic Acids Encoding the Single-chain Monellin Proteins

The present invention provides an isolated nucleic acid comprising a nucleotide sequence encoding a chimeric protein, said chimeric protein comprises, from N-terminus to C-terminus: a) a first peptidyl fragment consisting of an amino acid sequence that has at least 40% identity to residues 1–50 of the B chain of native monellin, in which the percentage identity is determined over an amino acid sequence of identical size to the B chain of native monellin; b) a peptidyl bond, or a second peptidyl fragment consisting of 1–12 amino acids; and c) a third peptidyl fragment consisting of an amino acid sequence that has at least 40% identity to residues 1–45 of the A chain of native monellin, in which the percentage identity is determined over an amino acid sequence of identical size to the A chain of native monellin, wherein said chimeric protein is stable and a given amount of said chimeric protein is at least 100-fold sweet as compared to the identical amount of sucrose, and within said nucleic acid, codons which are preferably used by yeast cells are used.

In a specific embodiment, the present invention provides an isolated nucleic acid comprising a nucleotide sequence encoding the chimeric protein wherein the first peptidyl fragment consists of an amino acid sequence that has at least 60% identity to the B chain of native monellin. Preferably, the first peptidyl fragment consists of an amino acid sequence that has at least 90% identity to the B chain of native monellin. More preferably, the first peptidyl fragment consists of the amino acid residues 1–50 of the B chain of native monellin.

In another specific embodiment, the present invention provides an isolated nucleic acid comprising a nucleotide sequence encoding the chimeric protein wherein the second peptidyl fragment consists of the amino acid sequence Gly-Gly-Gly-Ser-Gly-Gly-Gly-Ser-Gly-Gly-Gly-Ser (SEQ ID NO:1). Preferably, the second peptidyl fragment consists of the amino acid sequence Gly-Gly-Gly-Ser (SEQ ID NO:2). More preferably, the second peptidyl fragment consists of amino acid residue Gly.

In still another specific embodiment, the present invention provides an isolated nucleic acid comprising a nucleotide sequence encoding the chimeric protein wherein the third peptidyl fragment consists of an amino acid sequence that has at least 60% identity to the A chain of native monellin. Preferably, the third peptidyl fragment consists of an amino acid sequence that has at least 90% identity to the A chain of native monellin. More preferably, the third peptidyl fragment consists of the amino acid residues 1–45 of the A chain of native monellin.

In a preferred embodiment, the present invention provides an isolated nucleic acid comprising a nucleotide sequence encoding the chimeric protein wherein the first peptidyl fragment consists of the amino acid residues 1–50 of the B chain of native monellin, the second peptidyl fragment consists of the amino acid residue Gly and the third peptidyl fragment consists of the amino acid residues 1–45 of the A chain of native monellin.

In a specific embodiment, the present invention provides an isolated nucleic acid comprising a nucleotide sequence encoding the chimeric protein which is capable of being immunoreactively bound by an anti-monellin or an anti-thaumatin antibody.

In another specific embodiment, the present invention provides an isolated nucleic acid comprising a nucleotide sequence encoding the chimeric protein wherein the chimeric protein further comprises an amino acid sequence which is capable of directing secretion of said chimeric protein from *Pichia pastoris*. Preferably, the secretion-directing sequence is an endogenous signal sequence of *Pichia pastoris*. More preferably, the endogenous signal sequence is selected from the group consisting of the signal sequence of *Pichia pastoris* acid phosphatase, *Pichia pastoris* aspartic proteinase and *Pichia pastoris* carboxypeptidase Y encoded by *Pichia pastoris* PRC1. Alternatively, the secretion-directing sequence is a yeast signal sequence, wherein said yeast is not *Pichia pastoris*. Preferably, the yeast signal sequence is a signal sequence from *Saccharomyces cerevisiae*. More preferably, the *Saccharomyces cerevisiae* signal sequence is selected from the group consisting of the signal sequence of *Saccharomyces cerevisiae* SUC 2 and *Saccharomyces cerevisiae* mating pheromone α-factor. Most preferably, the *Saccharomyces cerevisiae* signal sequence is the signal sequence of *Saccharomyces cerevisiae* mating pheromone α-factor. Examples of other secretion-directing sequences that can be used in the present invention include, but are not limited to, the signal sequence of *Aspergillus giganteus* alpha-Sarcin, alpha-N-Acetylgalactosaminidase, OmpA protein, the mouse alpha-factor (cCell), the pepper endo-beta-1,4-glucanases, the laccase isolated from the ligninolytic fungus Tiametes, murine lysosomal acid alpha-mannosidase, the porcine inhibitor of carbonic anhydrase, *Aspergillus awamori* glucoamylase, mouse major urinary protein, pho1, rabbit angiolensin-converting enzyme (ACE), and the bacterial thermostable alpha amylase.

In a specific embodiment, the present invention provides an isolated nucleic acid comprising a nucleotide sequence encoding the chimeric protein which nucleic acid is a DNA. In another specific embodiment, the present invention provides an isolated nucleic acid which is hybridizable to the DNA sequence encoding the chimeric protein. In still another specific embodiment, the present invention provides an isolated nucleic acid comprising a nucleotide sequence complementary to the nucleotide sequence encoding the chimeric protein.

In a specific embodiment, the present invention provides a DNA encoding the chimeric protein which DNA further comprises a promoter which is capable of directing protein expression in *Pichia pastoris*. Preferably, the promoter is an endogenous promoter of *Pichia pastoris*. More preferably, the endogenous promoter is the promoter of *Pichia pastoris* glyceraldehyde-3-phosphate dehydrogenase (GAP). Alternatively, although not preferred, promoters of methanol responsive genes in methylotrophic yeast can also be used. Examples of such methanol responsive promoters include, but are not limited to, the promoter for the primary alcohol oxidase gene from *Pichia pastoris* AOX1, the promoter for the secondary alcohol oxidase gene from *Pichia pastoris* AOX2, the promoter for the dihydroxyacetone synthase gene from *Pichia pastoris* (DAS), the promoter for the P40 gene from *Pichia pastoris*, the promoter for the catalase gene from *Pichia pastoris*, and the like (see U.S. Pat. No. 5,324,639).

In another specific embodiment, the present invention provides a DNA encoding the chimeric protein which DNA further includes sequences allowing for its replication and selection in bacteria. In this way, large quantities of the DNA fragment can be produced by replication in bacteria.

In a preferred embodiment, the present invention provides a DNA encoding the chimeric protein, wherein within the encoded chimeric protein, the first peptidyl fragment consists of the amino acid residues 1–50 of the B chain of native monellin, the second peptidyl fragment consists of the amino acid residue Gly and the third peptidyl fragment consists of the amino acid residues 1–45 of the A chain of native monellin, and said DNA further comprises the promoter of *Pichia pastoris* GAP and the signal sequence of *Saccharomyces cerevisiae* mating pheromone α-factor.

In another preferred embodiment, the present invention provides a DNA encoding the chimeric protein, wherein the codons which arc preferably used by *Pichia pastoris* cells are used.

Figure 1:
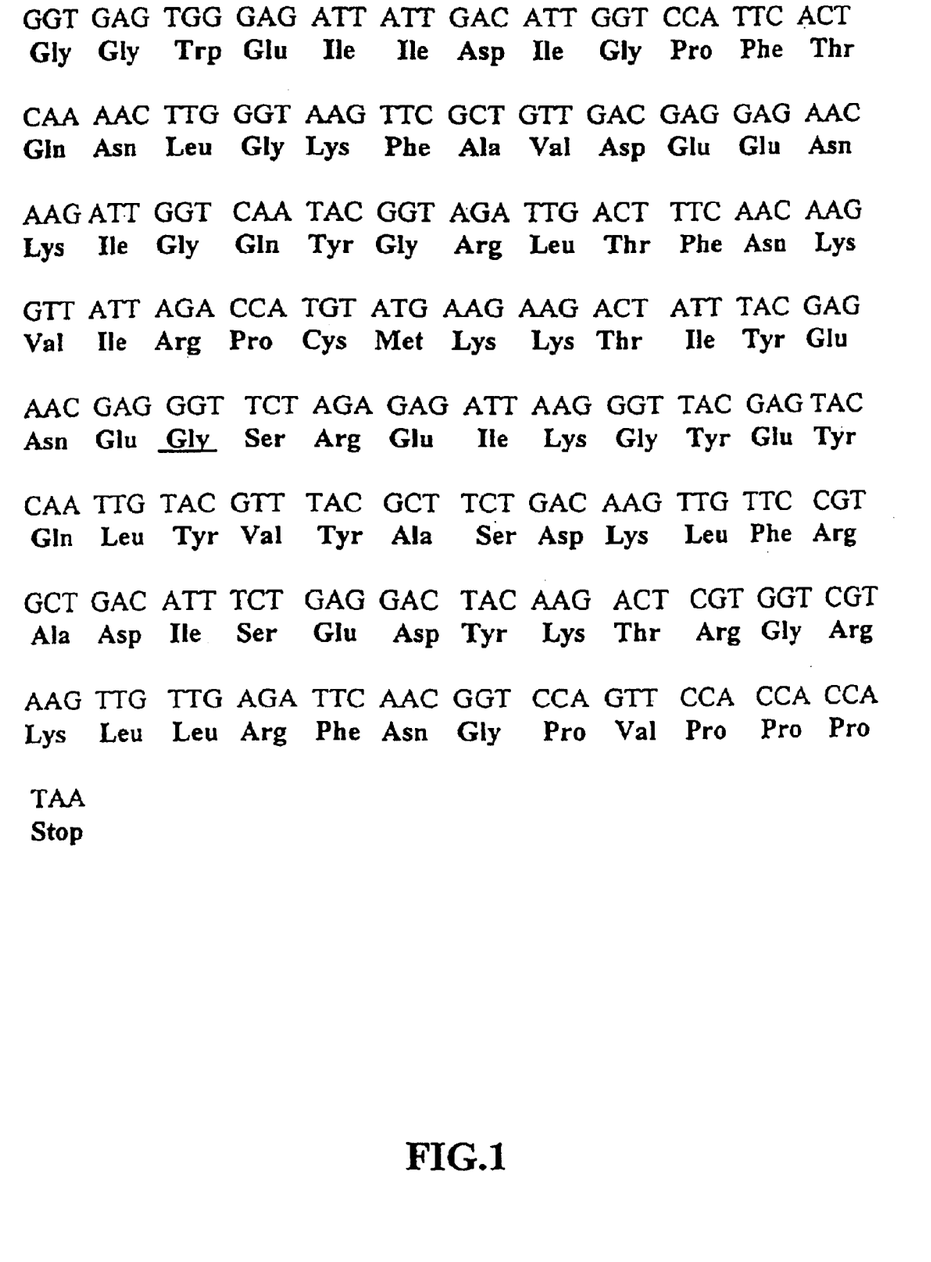
FIG. 1 shows the amino acid sequence of a recombinant single-chain monellin protein (SEQ ID NO:5) and the DNA sequence encoding the recombinant single-chain monellin protein (SEQ ID NO:6). Amino acid residues 1–50 corresponds to the amino acid residues 1–50 of the B chain of native monellin; amino acid residue 51 is Glycine as the linker; and amino acid residues 52–96 correspond to the amino acid residues 1–45 of the A chain of native monellin.
Figure 4:
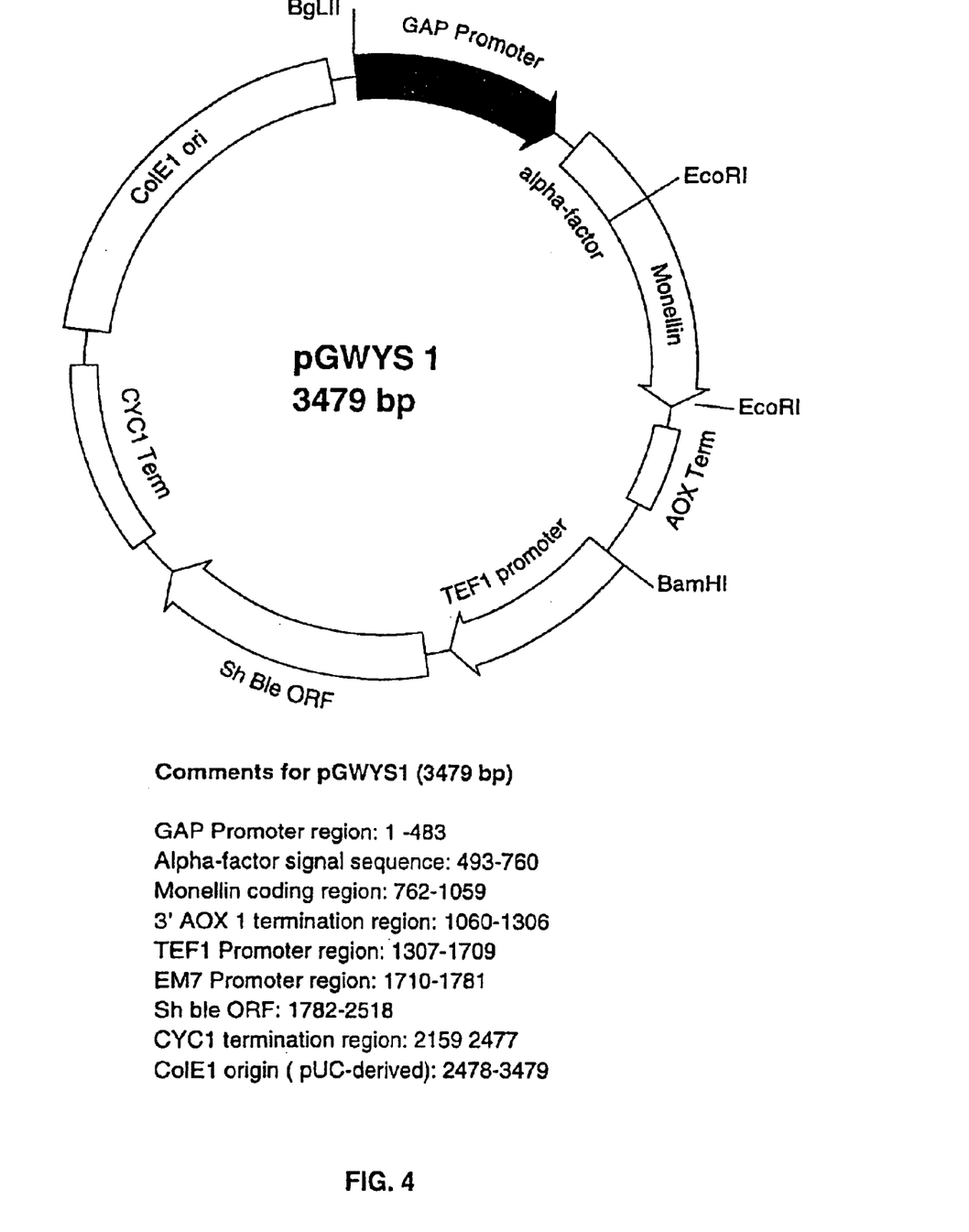
FIG. 4 shows the restriction map of recombinant monellin protein expression vector pGWYS1.

In a most preferred embodiment, the present invention provides a DNA encoding the chimeric protein wherein the DNA molecule comprises nucleotide sequence as depicted in FIG. 1 or the DNA vector as depicted in FIG. 4.

The nucleic acid comprising a nucleotide sequence encoding the chimeric protein disclosed herein, or any fragments, analogues or derivatives thereof, can be obtained by any method(s) known in the art. The nucleic acid may be chemically synthesized entirely. Alternatively, the nucleic acid encoding each fragment of the chimeric protein, i.e., the first, second or third peptidyl fragment, may be obtained by molecular cloning or may be purified from the desired cells. The nucleic acid encoding each fragment of the chimeric protein may then be chemically or enzymatically ligated together to form the nucleic acid comprising a nucleotide sequence encoding the chimeric protein disclosed herein, or any fragments, analogues or derivatives thereof.

Any *Dioscoreophyllum comminisii* cell potentially can serve as the nucleic acid source for the isolation of the nucleic acids encoding monellin. Alternatively, the nucleic acids encoding monellin can be designed and synthesized according to the amino acid sequence of the native monellin depicted in FIG. 1 (see also U.S. Pat. No. 5,478,923).

The DNA may be obtained by standard procedures known in the art from cloned DNA (e.g., a DNA "library"), by chemical synthesis, by cDNA cloning, or by the cloning of genomic DNA, or fragments thereof, purified from the desired cell (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) Clones derived from genomic DNA may contain regulatory and intron DNA regions in addition to coding regions; clones derived from cDNA will contain only exon sequences. Whatever the source, the gene should be molecularly cloned into a suitable vector for propagation of the gene.

In the molecular cloning of the gene from cDNA, cDNA is generated from totally cellular RNA or mRNA by methods that are well known in the art. The gene may also be obtained from genomic DNA, where DNA fragments are generated (e.g., using restriction enzymes or by mechanical shearing), some of which will encode the desired gene. The linear DNA fragments can then be separated according to size by standard techniques, including but not limited to, agarose and polyacrylamide gel electrophoresis and column chromatography.

Once a nucleic acid comprising a nucleotide sequence encoding the chimeric protein disclosed herein, or any fragments, analogues or derivatives thereof, has been obtained, its identity can be confirmed by nucleic acid sequencing (by any method well known in the art) and comparison to the known sequences. DNA sequence analysis can be performed by any techniques known in the art, including but not limited to the method of Maxam and Gilbert (Maxam and Gilbert, 1980, *Meth. Enzymol.*, 65:499–560), the Sanger dideoxy method (Sanger et al., 1977, *Proc. Natl. Acad. Sci. U.S.A.*, 74:5463), the use of T7 DNA polymerase (Tabor and Richardson, U.S. Pat. No. 4,795,699), use of an automated DNA sequenator (e.g., Applied Biosystems, Foster City, Calif.) or the method described in PCT Publication WO 97/15690.

Nucleic acids which are hybridizable to a nucleic acid comprising a nucleotide sequence encoding the chimeric protein disclosed herein, or any fragments, analogues or derivatives thereof, can be isolated, by nucleic acid hybridization under conditions of low, high, or moderate stringency (See also Shilo and Weinberg, 1981, *Proc. Natl. Acad. Sci. USA*, 78:6789–6792).

As used herein, "stable" means that a claimed single-chain monellin chimeric protein retains at least 70% or its sweet intensity after the protein has been placed at about 4° C. for at least 6 months, or at about 60° C. for at least 2.5 hours, or at about 100° C. for at least 5 minutes. In addition, "stable" means that a claimed single-chain moneflin chimeric protein retains at least 70% of its sweet intensity after the protein has been placed at a pH raging from about 2.0 to about 11.0 for at least 6 hours.

Sweetness of the claimed single-chain monellin chimeric protein can be assessed using an ordinary taste test that is known in the art. For example, comparison to the sweetness of sucrose can be made by suitable dilutions on a weight basis (see also U.S. Pat. No. 5,478,923).

The preferred codon usage by yeast cells can be determined by methods known in the art, e.g., methods disclosed in Sharp et al., *Nucleic Acids Res.*, 1986, 14(13);5125–43 and in Li and Luo, *J. Theor. Biol.*, 1996, 181(2):111–24. According to Sharp, important characteristics of the preferred codon in yeast include a higher correlation with tRNA abundance, a greater degree of third base pyrimidine bias, and a lesser tendency to the A+T bas pairs. Li and Luo discloses a method of classifying and predicting the gene expression level in *E. coli* and yeast cells which is called the Self-Consistent Information Clustering (SCIC). Using the modified Codon Adaption Index (CAI) values, Li and Luo have accomplished the linear regression analysis on the relation between base composition, base correlation and gene expression level in *Escherichia coli* and yeast. Li and Luo also proposed the assumption of Expression-Enhancing-Network Site (EENS), the existence of which can be demonstrated by the linear equations between gene expression and base correlations in a codon, in adjacent codons and in non-adjacent codons. In addition, the codons that have been successfully used for expressing heterologous proteins in *Pichia pastoris* cells can be used. Examples of such codons can be found in U.S. Pat. No. 4,837,148; U.S. Pat. No. 4,855,231; U.S. Pat. No. 4,882,279; U.S. Pat. No. 4,929,555; U.S. Pat. No. 5,122,465; U.S. Pat. No. 5,324,639; Martinez-Ruiz et al., *Protein Expr. Purif.*, 1998, 12(3): 315–22; Abdulaev et al., *Protein Expr. Purif.*, 1997, 10(1): 61–9; Kotake et al., *J. Lipid Res.*, 1996, 37(3):599–605; Zhu et al., *Arch. Biochem. Biophys.*, 1998, 352(1);1–8; Heim et al., *Biochim. Biophys. Acta.*, 1998, 1396(3):306–19; Ferrarese et al., *FEBS Lett.*, 1998. 422(1):23–6; Jonsson et al., *Curr. Genet.*, 1997, 32(6):425–30; Merkle et al., *Biochim. Biophys. Acta.*, 1997, 1336(2):132–46; Wuebbens et al., *Biochemistry.*, 1997, 36(14):4327–36; Fierobe et al., *Protein Expr. Purif*, 1997, 9(2):159–70; Ferrari et al., *FEBS Lett.*, 1997, 401(1):73–7; Skory et al., *Curr. Genet.*, 1996, 30(5): 417–22; Sadhukhan et al., *J. Biol. Chem.*, 1996, 271(31): 18310–3; Tsujikawa et al., *Yeast*, 1996, 12(6):541–53; Ohi et al., *Yeast*, 1996, 12(1):31–40; Paifer et al., *Yeast*, 1994, 10(11):1415–9; Fidler et al., *J. Mol. Endocrinol.*, 1998, 21(3):327–336; and Brocca et al., *Protein Sci.*, 1998, 7(6): 1415–22.

Whether a chimeric protein is capable of being immunoreactively bound by an anti-monellin or an anti-thaumatin antibody can be determined by methods known in the art. The examples of anti-monellin or an anti-thaumatin antibodies that can be used in the present invention include, but are not limited to, the antibodies disclosed in Slootstra et al., *Chem. Senses*, 1995, 20(5):535–43; Antonenko and Zanetti, *Life Sci.*, 1994, 55(15):1187–92; Bodani et al., *Hybridoma*, 1993, 12(2):177–83; Mandal et al., *Hybridoma*, 1991, 10(4): 459–66 and Haimovich, *Isr. J. Med. Sci.*, 1975, 11(11):1183.

5.2. Production of Monellin Proteins from Recombinant *Pichia Pastoris* Cells In a specific embodiment, the present invention provides a recombinant *Pichia pastoris* cell containing the nucleic acid which encodes a chimeric protein, said chimeric protein comprises, from N-terminus to C-terminus: a) a first peptidyl fragment consisting of an amino acid sequence that has at least 40% identity to residues 1–50 of the B chain of native monellin, in which the percentage identity is determined over an amino acid sequence of identical size to the B chain of native monellin; b) a peptidyl bond, or a second peptidyl fragment consisting of 1–12 amino acids; and c) a third peptidyl fragment consisting of an amino acid sequence that has at least 40% identity to residues 1–45 of the A chain of native monellin, in which the percentage identity is determined over an amino acid sequence of identical size to the A chain of native monellin, wherein said chimeric protein is stable and a given amount of said chimeric protein is at least 100-fold sweet as compared to the identical amount of sucrose, and within said nucleic acid, codons which are preferably used by yeast cells are used. Preferably, the recombinant *Pichia pastoris* cell contains a DNA molecule comprises nucleotide sequence as depicted in FIG. 1 or a DNA vector as depicted in FIG. 4. Recombinant *Pichia pastoris* cells containing the nucleic acids disclosed in Section 4.1, are also provided.

Methods for transforming methylotrophic yeast, such as *Pichia pastoris*, as well as methods applicable for culturing methylotrophic yeast cells containing in their genome a gene encoding a heterologous protein, are known generally in the art. Preferably, the transformation, positive transformant selection and culturing methods disclosed in U.S. Pat. No. 4,837,148; U.S. Pat. No. 4,855,231; U.S. Pat. No. 4,882,279; U.S. Pat. No. 4,929,555; U.S. Pat. No. 5,122,465; U.S. Pat. No. 5,324,639 can be used in the present invention.

In another specific embodiment, the present invention provides a process for producing a monellin chimeric protein comprising growing a recombinant *Pichia pastoris* cell containing the nucleic acid disclosed in Section 4.1, such that the encoded chimeric protein is expressed and secreted by the cell, and recovering the expressed and secreted chimeric protein. Preferably, the recombinant *Pichia pastoris* cell containing a DNA molecule comprises nucleotide sequence as depicted in FIG. 1 or a DNA vector as depicted in FIG. 4 is used.

Any suitable fermentation process in the art can be used in the present process. For large-scale production of recombinant DNA-based products driven by a GAP promoter in methylotrophic yeast such as *Pichia pastoris*, a three-stage, high cell-density fed batch fermentation system is preferably employed. In the first or growth stage of this fermentation system, the expression host *Pichia pastoris* cells are cultured in defined minimal medium such as BMGY (Buffered Minimal Glycerol-complex medium) with an excess of a non-inducing carbon source (e.g., glycerol). When the expression host *Pichia pastoris* cells are grown on such carbon sources, heterologous gene expression is repressed, which allows the generation of cell mass in the absence of heterologous protein expression. During this growth stage, it is also preferred that the pH of the medium be maintained at about 5. Next, the expression host *Pichia pastoris* cells are grown on limited non-inducing carbon source for a short period of time to further increase the cell mass and to depress the glucose responsive promoter. The pH of the medium during this limited growth period is kept below 4, preferably in the range from about 2.0 to about 3.5. The final stage is the production stage wherein either the "glucose excess fed-batch mode" or the "mixed-feed fed-batch mode" can be used. In the "glucose excess fed-batch mode," 2% glucose alone is added. In the "mixed-feed fed-batch mode," a limiting amount of a non-inducing carbon source and glucose is added in the fermentor to induce the expression of the monellin gene driven by a GAP promoter.

The secreted monellin chimeric proteins can be recovered from the *Pichia pastoris* culture medium by any methods known in the art. For example, methods disclosed in U.S. Pat. Nos. 3,878,184 and 3,998,798; Morris and Cagan, *Biochim. Biophys. Acta*, 1972, 261:114–122; Kim et al., *Protein Eng.*, 1989, 2:571–575; and Recently, Kondo et al., *Nature Biotechnology*, 1997, 15:453–457 can be used for recovering and isolating the secreted monellin chimeric proteins. Preferably, the expressed and secreted chimeric protein is recovered by a means comprising ion-exchange chromatography. More preferably, the expressed and secreted chimeric protein is recovered by a means comprising CM-Sephadex column chromatography or DEAE-Sephadex column chromatography.

In another specific embodiment, the present invention provides the product of the above processes.

6. EXAMPLE

6.1. Preparation of the Synthetic Recombinant Monellin DNA

The amino acid sequence of the recombinant monellin protein and the nucleotide sequence of the DNA encoding the recombinant monellin protein are shown in FIG. 1. As shown in FIG. 1, nucleotides 1–150 encode residues 1–50 of the B chain of the native monellin protein; nucleotides 150–152 encode Glycine as the linking "L" portion; and nucleotides 153–287 encode residues 1–45 of the A chain of the native monellin protein. The recombinant monellin protein is preceded by the following amino acid sequence, which corresponds to a Met residue and the signal sequence of *Saccharomyces cerevisiae* mating pheromone α-factor:Met-Leu-Leu-Phe-Ile-Asn-Thr-Thr-Ile-Ala-Ser-Ile-Ala-Ala-Lys-Glu-Glu-Gly-Val-Ser-Leu-Glu-Lys-Arg-Glu-Ala-Glu-Ala-Glu-Phe (SEQ ID NO:3).

Figure 2:
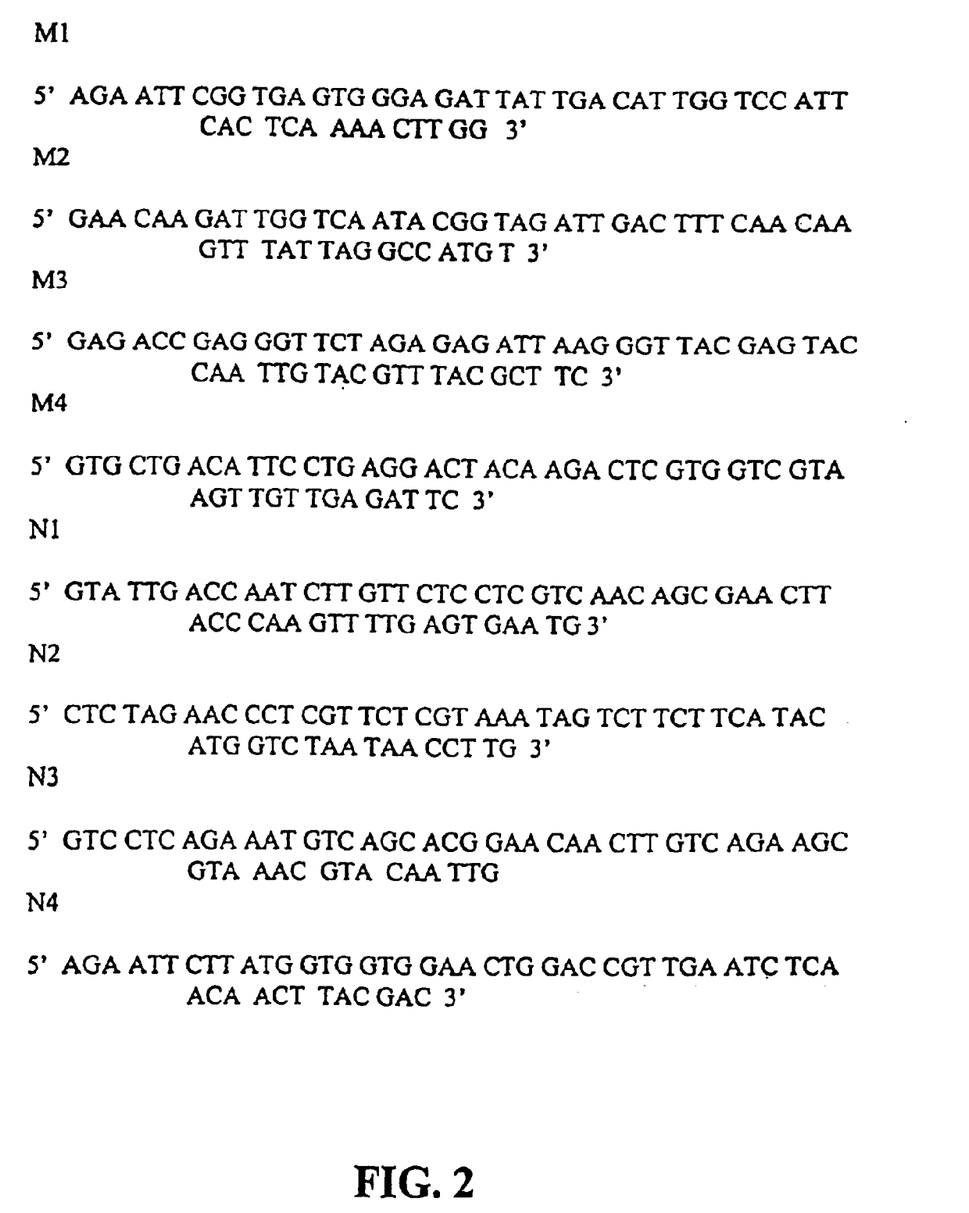
FIG. 2 shows the DNA sequences of the oligos which were used for synthesis of the recombinant single-chain monellin protein (SEQ ID NOs:7–14).
Figure 3:
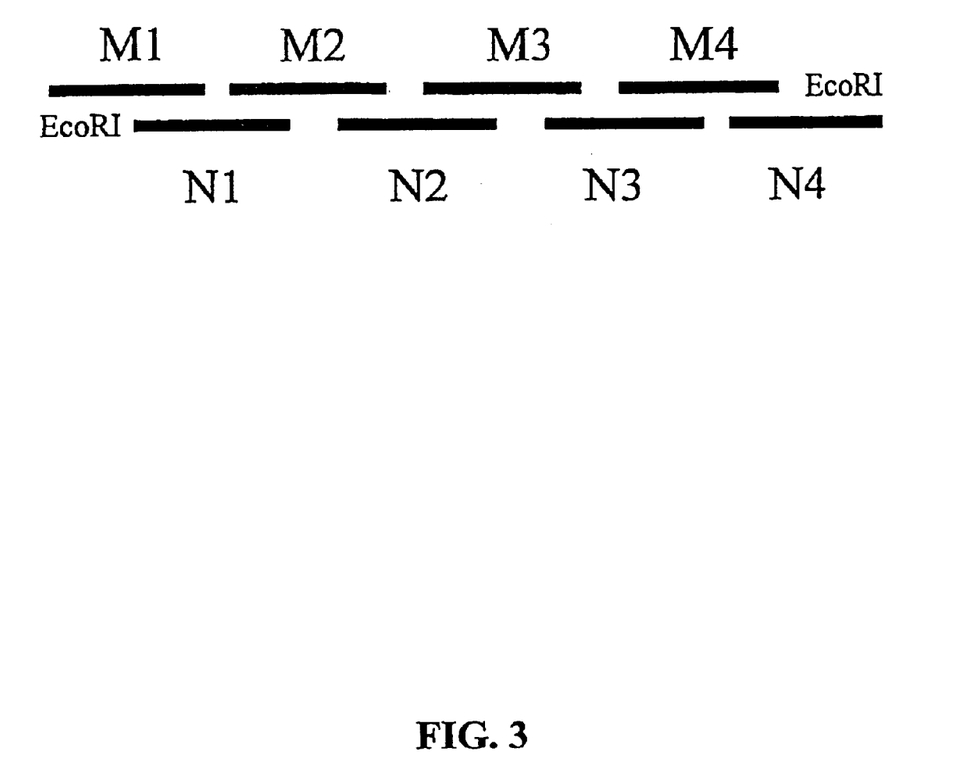
FIG. 3 shows the location of each of DNA oligo in the synthesized monellin DNA and its enzymatic digestion sites.
Figure 5:
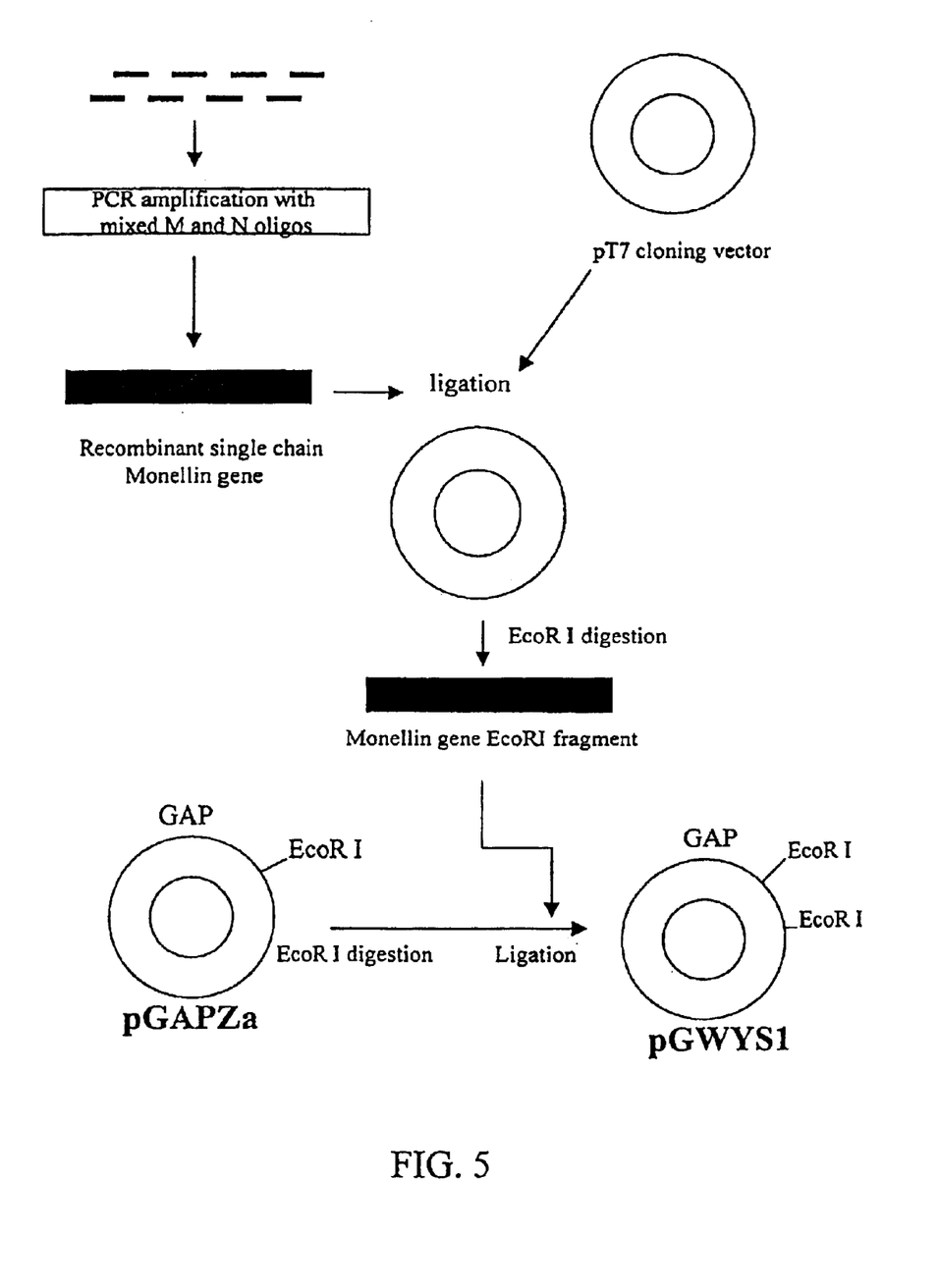
FIG. 5 shows the construction of pGWYS1.
Figure 6:
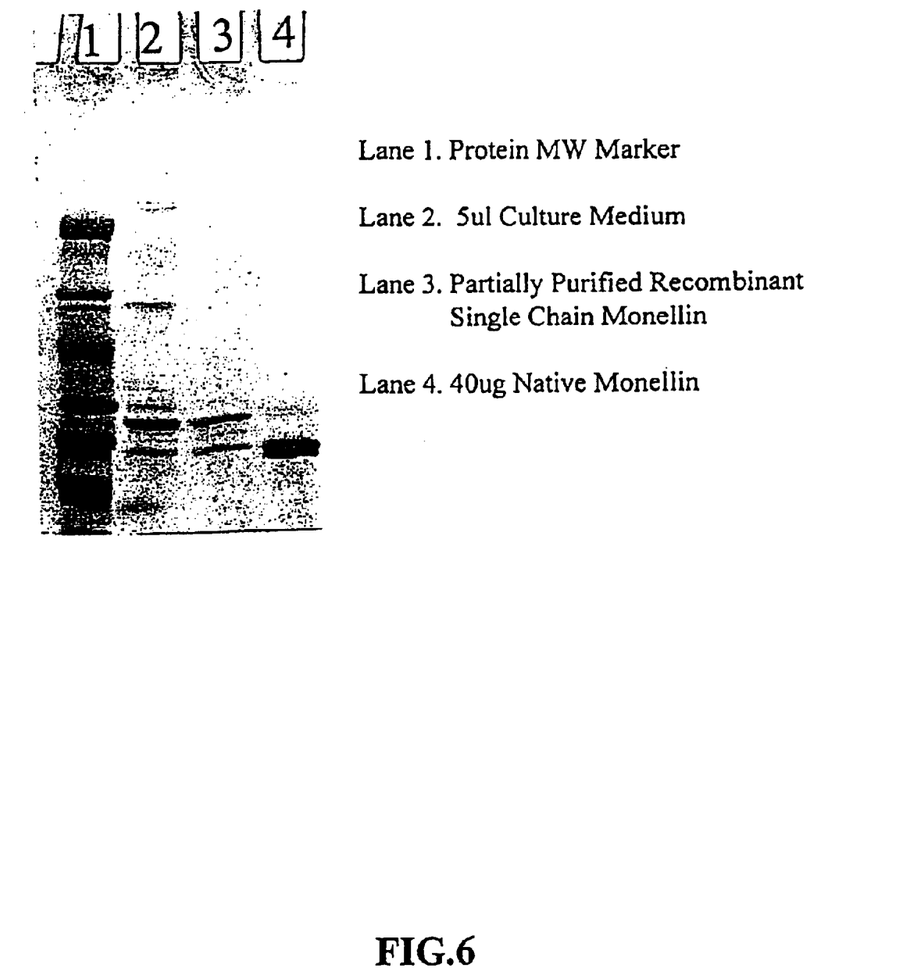
FIG. 6 shows the SDS-PAGE analysis of the secreted recombinant monellin protein isolated from the culture medium.
Figure 7A:
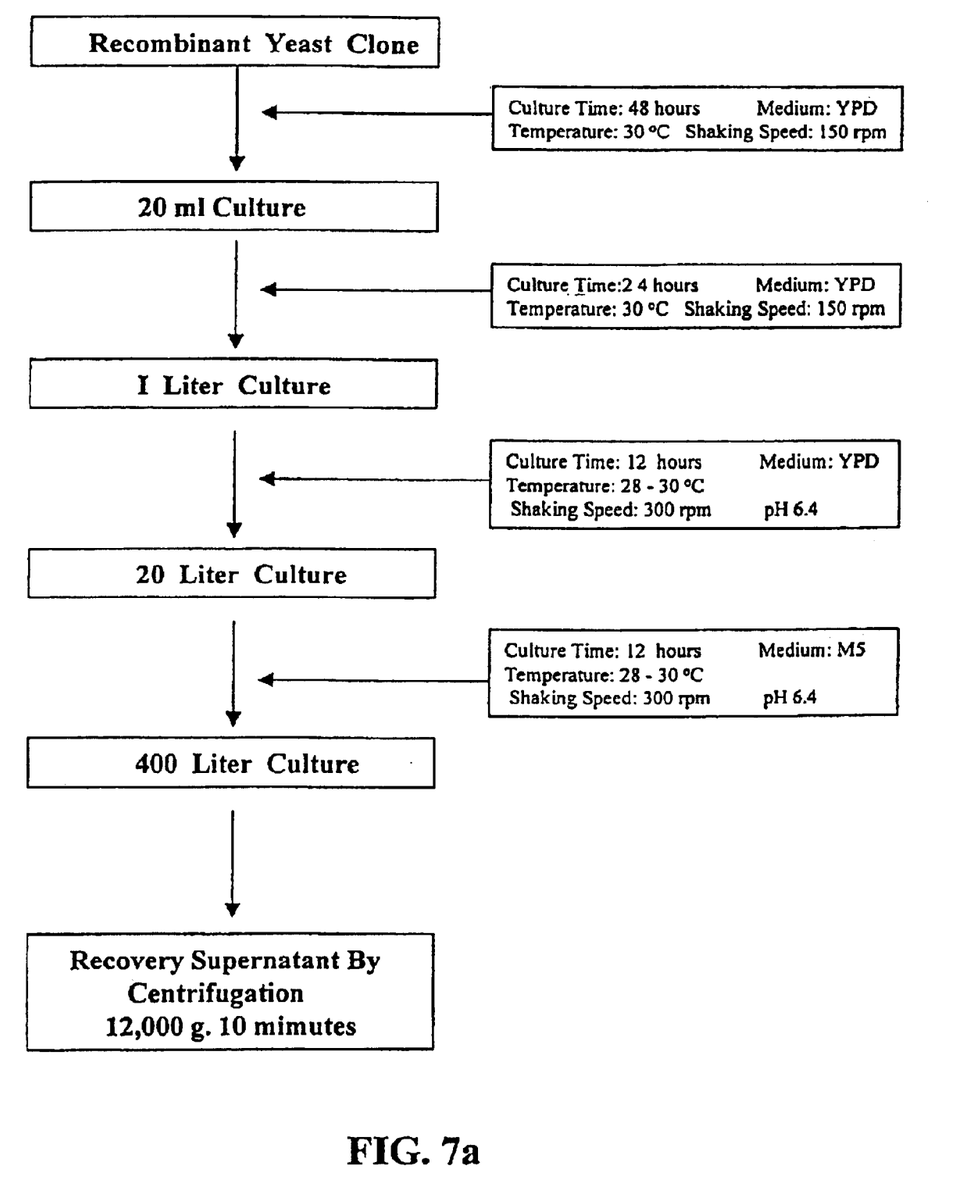
FIG. 7 shows the steps for purifying the secreted recombinant monellin protein.
Figure 7B:
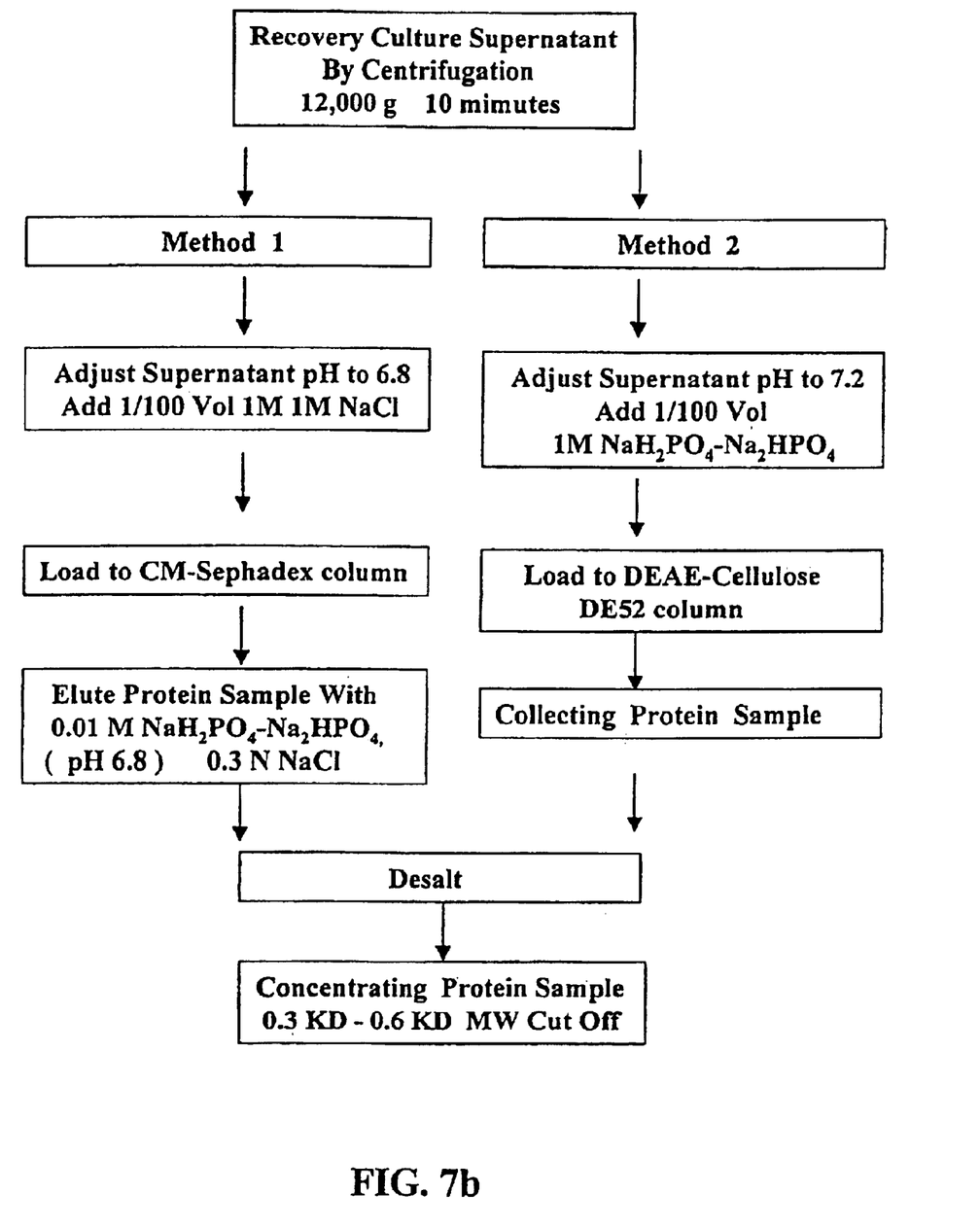

This synthetic DNA encoding the signal sequence of *Saccharomyces cerevisiae* mating pheromone α-factor and the recombinant monellin protein was prepared from the oligos M1–M4 and N1–N4, which were synthesized using the Applied Biosystems 380B DNA Synthesizer by ACTG company (see FIGS. 2–3 and 5). The oligos were isolated by urea-polyacrylamide gel electrophoresis and purified by passing through a Sep-pak C18 column (Whatman) and annealed and ligated as shown in FIG. 3 to obtain the synthetic DNA bracketed by EcoRI sites.

To synthesize the DNA encoding the signal sequence of *Saccharomyces cerevisiae* mating pheromone α-factor and the recombinant monellin protein, in 100 ul PCR reaction volume, 2 pM of each of the oligo M2 to N3 were mixed with 10 pM M1 and N4, heated to 94° C. for 5 minutes in the absence of Taq DNA polymerase. The reaction mixture was then slowly cooled down to 37° C. After 1 unit of the Vent DNA polymerase (New England Biolabs, Inc.) was added, the PCR reaction was performed according to the standard protocol. One hundred microliter PCR reaction mixture contains 50 mM Tris-HCl (pH 8.0), 2.5 mM MgCl$_2$, 10 mM DTT, 1 mM dNTP, and 1 unit of the Vent DNA polymerase. The PCR reaction was performed as following: at 94° C. for 1 minute, 53° C. for 1.5 minutes, 72° C. for 2 minutes within each cycle; and for a total of 30 cycles. Finally, the reaction mixture was incubated at 72° C. for 10 minutes. The reaction mixture was extracted by phenol/chloroform, precipitated with ethanol, and gel purified in 1.2% low-melting agarose gel. The purified DNA fragment was inserted into the pT7bleu (R) vector (Novagen, Inc.) to generate the pT7yM plasmid (see FIG. 5). In 20 ul DNA ligation reaction, 2 ul of 10 mM ATP, 40 units of the T4 DNA ligase (New England Biolab, Inc.) was added and mixed with 1 ug purified monellin DNA fragment and 50 ng pT7blue (R) vector. The reaction mixture was kept at 16° C. for 16 hours. The ligation mixture was transformed into host cells by adding 5 ul of the ligation mixture to 200 ul of *E. coli* NovaBlue competent cells (Messing, *Methods in Enzymology*, 1983, 101:20–78) and the desired sequence was confirmed by dideoxy sequencing using T7 and U19 primer (Sanger et al., *Proc. Natl. Acad. Sci.*, 1985, 74:5463–5467). (1)

6.2. Preparation of the Expression Vector pGWYS-1

The pGAPZa expression vector was purchased from Invitrogen, Inc. The synthetic monellin DNA fragment was removed from pT7yMenallin with EcoRI and inserted into an EcoRI site of the pGAPZa vector to give pGWYS. Briefly, 5 ug purified pT7yMenallion plasmid was digested in 20 ul reaction volume using 5 units EcoRI (Promega Inc.) at 37° C. for 2 hours. After the reaction mixture was separated by 1% low-melting agarose gel electrophoresis, the synthetic monellin DNA fragment was purified using the Wizard PCR Preps DNA purification kit (Promega, Inc). One hundred ng purified monellin DNA fragment were used for ligation into the expression pGAPZa vector. In the 10 ul ligation reaction, 50 ng of the EcoRI digested pGAPZa vector was mixed with 100 ng purified monellin DNA fragment. The ligation reaction was carried out in the presence of 10 ul of 20 mM Tris-HCl (pH 7.5), 10 mM MgCl, 10 mM DTT and 200 units of the T4 DNA ligase (New England Biolabs, Inc.) at 16° C. overnight to give the pGWYS. The ligation mixture was transformed into *E. coli* TOP10F' cells (Invitrogen, Inc.). Twenty Zeocin-resistant clones were picked and orientation of the insert was screened by PCR reaction using the α-factor (5' CTATTGCCAGCATTGCTGC3') (SEQ ID NO:4) and the N4 oligos. Each selected clone was transferred into 3 ml culture medium containing 200 ug/ml Zeocin and incubated with shaking at 37° C. overnight. The recombinant plasmid pGWYS was prepared from 1.5 ml cultured bacteria cells using the Qiagen Tip 20 kit system (Qiagen, Inc.). Fifty ng purified pGWYS plasmid was used as the PCR template to determine orientation of the insert. In 25 ul PCR reaction, 50 ng of the pGWYS plasmid was mixed with 2.5 pM of the α-factor and the N4 oligos in the presence of 1 unit Taq DNA polymerase (Promega, Inc.). The PCR reaction was performed under the following conditions: at 94° C. for 1 minute, 55° C. for 1 minute, 72° C. for 2 minutes within each cycle; and for a total of 40 cycles. Finally, the reaction mixture was incubated at 72° C. for 10 minutes. After the PCR reaction mixture was separated on 1.2% agarose gel, one of the clones which contains the insert with the desired orientation was named pGWYS-1. The sequence of the insert was further confirmed by DNA sequencing.

6.3. Transformation of *Pichia pastoris* Cells with the pGWYS-1

To generate the high-level and stable expression of monellin in *Pichia pastoris*, purified pGWYS-1 plasmid was transformed into *Pichia pastoris* cells by electroporation technique described in the *Pichia pastoris* Expression Kit Manual using the Electroporation Apparatus II (Invitrogen Inc.). Briefly, 500 ml of the *Pichia pastoris* GS115 cells were grown in YPD medium at 30° C. to an $OD_{600}$ of 1.3. Cells were pelleted with a centrifugation of 1,500 g for 5 minutes at 4° C. Pelleted cells were washed with 500 ml of ice-cold sterile water. The washing step was repeated with 250 ml and 20 ml ice-cold sterile water, receptively. Then, the cells were washed with 20 ml of ice-cold 1 M sorbitol and resuspend in 1 ml ice-cold sorbitol. Forty ul of the yeast GS115 cells in 1 M sorbitol were mixed with 10 ug purified pGWYS-1 plasmid to total volume 50 ul and the mixture was transferred into an ice-cold cuvette. The cuvette containing the mixture was incubated on ice for 5 minutes. Electroporation was performed according to the Electroporation Apparatus II manual parameters (Invitrogen Inc manufacture). After the electrical pulse, 1 ml of ice-cold 1M sorbitol was added into the cuvette, and the content of the cuvette was transferred into a microcentrifuge tube. Two hundred ul transformed cells were plated on one 5 RDB plate containing 400 ug/ml Zeocin. The plates were incubated at 30° C. until colonies appeared. Positive transformants were characterized by their growth in the presence of Zeocin at various concentrations, e.g., 400 ug/ml, 600 ug/ml, 800 ug/ml and 1000 ug/ml.

6.4. Stability Test of the Positive Transformants

Three positive transformants were selected for further characterization based on their growth in the presence of 800 ug/ml Zeocin and the expression of recombinant monellin by the 2% glucose induction. The following experiment was performed to test their genetic stability. Each of these 3 positive transformants was picked up using a sterile toothpick and incubated on a YPD plate without any selection at 30° C. until colonies appeared. The colonies were picked up and plated on a new YPD plate until new colonies appeared. After such non-selective growth was repeated 50 times, each of the passage colonies was incubated on a selective plate containing 800 ug/ml Zeocin. The protein expression upon 2% glucose induction was analyzed by SDS-PAGE. All three positive transformants showed the same phenotype as the original colonies after 50 times passage on the YPD plates.

6.5 Production of the Recombinant Monellin Protein

Each of the three positive transformants selected in 5.4, was grown in1 liter YPD medium in 5 liter flask at 30° C. with vigorous shaking (250 rpm). Two ml supernatant were obtained from the culture after 24 hours, 48 hours and 72 hours, respectively. Five ul of the samples collected at each time point were analyzed using the 15–20% gradient polyacrylamide gel. The secreted recombinant monellin protein was observed as the 12 kD protein band. Quantitation of the SDS-PAGE analysis using the Densitometer (Molecular Dynamic, Inc.) indicates that one of the positive strain produced nearly 10 grams per liter secreted recombinant single-chain monellin protein. This strain was named GWyS1.

6.6 Purification of Secreted Recombinant Monellin Protein

Protein methods were used to purify the recombinant monellin protein secreted from GwyS-1 yeast strain. According to the first method, after 72-hour culturing, supernatant was collected by a centrifugation at 12,000 rpm (17,000 g). After collection, the supernatant pH was adjusted to about 6.8 using 0.1 N NaOH solution. One M $NaH_2PO_4$—$Na_2HPO_4$ (pH6.8) was added into the supernatant till 1:100

(v/v) and mixed well. The supernatant was then loaded on the CM-Sephadex column (Phamacia, Inc.) pre-equilibrated with 0.01 M $NaH_2PO_4$—$Na_2HPO_4$ (pH6.8) solution. After the column was washed with 5 column volume 0.01 M $NaH_2PO_4$—$Na_2HPO_4$ (pH6.8) solution, the recombinant monellin protein was eluted with 0.3 M NaCl-0.01 M $NaH_2PO_4$—$Na_2HPO_4$ (pH6.8) solution. After dialysis against water, the purity of the protein was determined to be about 98% by gel electrophoresis.

According to the second method, after 72-hour culturing, supernatant was collected by a centrifugation at 12,000 rpm (17,000 g). After collection, the supernatant pH was adjusted to about 7.2 using 0.1 N NaOH solution. One M NaCl-1 M $NaH_2PO_4$—$Na_2HPO_4$ (pH 7.2) was added into the supernatant till 1:100 (v/v) and mixed well. The supernatant was then loaded on the DEAE-Sephadex column (Phamacia, Inc.) pre-equilibrated with 1 M $NaH_2PO_4$—$Na_2HPO_4$ (pH 7.2)-1M NaCl solution. The flow-through fraction was collected and dialyzed against water. The purity of the protein was determined to be about 98% by gel electrophoresis.

The recombinant monellin protein purified according to either method was further lyophilized to dry powder for testing its sweetness.

6.7. Sweetness and Stability Test

Sweetness of the purified recombinant monellin protein was assessed using an ordinary taste test. Comparison to the sweetness of sucrose was made by suitable dilutions on a weight basis. In a typical test, 1, 10, 25 and 50 mg/ml aqueous sucrose solutions were used as standard solutions. The minimum weight of the purified recombinant monellin protein which could generate sweet taste was compared with that of sucrose. The recombinant monellin of this invention requires the addition of an amount which is about 1000-fold less than that of sucrose. For example, 50 ng/ml recombinant monellin protein solution was as sweet as 50 mg/ml sucrose (Lucky Supermarket's Lady Lee brand sugar).

Stability was measured by dissolving natural monellin (Sigma, Inc.) and the purified recombinant monellin protein at 100 ug/ml concentration at pH 2.0, 4.0, 6.3. and 7.5. Each sample was heated to 37° C., 50° C., 60° C., 70° C., 80° C., 90° C. and 100° C. for 15 minutes and let cool to room temperature before tasting. The most dramatic difference was that natural monellin lost its sweetness when heated to 50° C. at pH 2.0, while the purified recombinant monellin protein retained its sweetness even after heating at 100°0 C. for 5 minutes.

The present invention is not to be limited in scope by the microorganism deposited or the specific embodiments described herein. Indeed, various modifications of the invention in addition to those described herein will become apparent to those skilled in the art from the foregoing description and accompanying figures. Such modifications are intended to fall within the scope of the appended claims.

Various references are cited herein, the disclosures of which are incorporated by reference in their entireties.

What is claimed is:

1. An isolated nucleic acid comprising a nucleotide sequence encoding a chimeric protein, which nucleic acid encodes the amino acid residues 1–96 set forth in SEQ ID NO:5.

2. The isolated nucleic acid of claim 1, wherein the chimeric protein further comprises an amino acid sequence which is capable of directing secretion of said chimeric protein from *Pichia pastoris*.

3. The isolated nucleic acid of claim 2, wherein the secretion directing sequence is an endogenous signal sequence of *Pichia pastoris*.

4. The isolated nucleic acid of claim 3, wherein the endogenous signal sequence is selected from the group consisting of the signal sequence of *Pichia pastoris* acid phosphatase, *Pichia pastoris* aspartic proteinase and *Pichia pastoris* carboxypeptidase Y encoded by *Pichia pastoris* PRC1.

5. The isolated nucleic acid of claim 2, wherein the secretion-directing sequence is a yeast signal sequence, wherein said yeast is not *Pichia pastoris*.

6. The isolated nucleic acid of claim 5, wherein the yeast signal sequence is a signal sequence from *Saccharomyces cerevisiae*.

7. The isolated nucleic acid of claim 6, wherein the *Saccharomyces cerevisiae* signal sequence is selected from the group consisting of the signal sequence of *Saccharomyces cerevisiae* SUC 2 and *Saccharomyces cerevisiae* mating pheromone α-factor.

8. The isolated nucleic acid of claim 7, wherein the *Saccharomyces cerevisiae* signal sequence is the signal sequence of *Saccharomyces cerevisiae* mating pheromone α-factor.

9. The isolated nucleic acid of claim 1, wherein the chimeric protein further comprises an amino acid sequence which is capable of directing secretion of said chimeric protein from *Pichia pastoris*.

10. The isolated nucleic acid of claim 9, wherein the secretion-directing sequence is the signal sequence of *Saccharomyces cerevisiae* mating pheromone α-factor.

11. The isolated nucleic acid of claim 2, wherein the secretion-directing sequence is selected from the group consisting of the signal sequence of *Aspergillus gigantells* alpha-Sarcin, alpha-N-Acetylgalactosaminidase, OmpA protein, the mouse alpha-factor (cCell), the pepper endo-beta-1,4-glucanases, the laccase isolated from the ligninolytic fungus Trametes, murine lysosomal acid alpha-mannosidase, the porcine inhibitor of carbonic anhydrase, *Aspergillus awamori* glucoamylase, mouse major urinary protein, pho 1, rabbit angiotensin-converting enzyme (ACE), and the bacterial thermostable alpha amylase.

12. The isolated nucleic acid of claim 1, wherein said nucleic acid is a DNA.

13. An isolated nucleic acid comprising a nucleotide sequence fully complementary to the nucleotide sequence of claim 1.

14. An isolated nucleic acid hybridizable to the DNA sequence of claim 12.

15. The DNA of claim 12, further comprising a promoter which is capable of directing protein expression in *Pichia pastoris*.

16. The DNA of claim 15, wherein the promoter is an endogenous promoter of *Pichia pastoris*.

17. The DNA of claim 16, wherein the endogenous promoter is the promoter of *Pichia pastoris* glyceraldehyde-3-phosphate dehydrogenase.

18. The DNA of claim 12, said DNA further comprises the promoter of *Pichia pastoris* glyceraldehyde-3-phosphate dehydrogenase and the signal sequence of *Saccharomyces cerevisiae* mating pheromone α-factor.

19. The DNA of claim 12, wherein the codons which are preferably used by *Pichia pastoris* cells are used.

20. A DNA molecule comprises nucleotide sequence as set forth in SEQ ID NO:6.

21. A recombinant *Pichia pastoris* cell containing the nucleic acid of claim 1.

22. A recombinant *Pichia pastoris* cell containing the DNA of claim 20.

23. A process for producing a chimeric protein comprising growing a recombinant *Pichia pastoris* cell containing the nucleic acid of claim 1 such that the encoded chimeric protein is expressed and secreted by the cell, and recovering the expressed and secreted chimeric protein.

24. A process for producing a chimeric protein comprising growing a recombinant *Pichia pastoris* cell containing the DNA of claim 20 such that the encoded chimeric protein is expressed and secreted by the cell, and recovering the expressed and secreted chimeric protein.

25. The process of claim 23, wherein the expressed and secreted chimeric protein is recovered by a means comprising ion-exchange chromatography.

26. The process of claim 25, wherein the ion-exchange chromatography being used is CM-Sephadex column chromatography.

27. The process of claim 25, wherein the ion-exchange chromatography being used is DEAE-Sephadex column chromatography.

28. The product of the process of claim 23.
29. The product of the process of claim 24.
30. The product of the process of claim 25.
31. The product of the process of claim 26.
32. The product of the process of claim 27.
33. A chimeric protein, said chimeric protein comprises the amino acid residues 1–96 set forth in SEQ ID NO:5.

* * * * *

```
SEQUENCE LISTING

<160> NUMBER OF SEQ ID NOS: 14

<210> SEQ ID NO 1
<211> LENGTH: 12
<212> TYPE: PRT
<213> ORGANISM: Artificial Sequence
<220> FEATURE:
<223> OTHER INFORMATION: Peptidyl fragment of the chimeric protein

<400> SEQUENCE: 1

Gly Gly Gly Ser Gly Gly Gly Ser Gly Gly Gly Ser
1               5                   10

<210> SEQ ID NO 2
<211> LENGTH: 4
<212> TYPE: PRT
<213> ORGANISM: Artificial Sequence
<220> FEATURE:
<223> OTHER INFORMATION: Peptidyl fragment of the chimeric protein

<400> SEQUENCE: 2

Gly Gly Gly Ser
1

<210> SEQ ID NO 3
<211> LENGTH: 30
<212> TYPE: PRT
<213> ORGANISM: Saccharomyces cerevisiae

<400> SEQUENCE: 3

Met Leu Leu Phe Ile Asn Thr Thr Ile Ala Ser Ile Ala Ala Lys Glu
1               5                   10                  15

Glu Gly Val Ser Leu Glu Lys Arg Glu Ala Glu Ala Glu Phe
```

<210> SEQ ID NO 4
<211> LENGTH: 19
<212> TYPE: DNA
<213> ORGANISM: Artificial Sequence
<220> FEATURE:
<223> OTHER INFORMATION: alpha-factor

<400> SEQUENCE: 4
ctattgccag cattgctgc                                                19

<210> SEQ ID NO 5
<211> LENGTH: 96
<212> TYPE: PRT
<213> ORGANISM: Pichia pastoris

<400> SEQUENCE: 5

Gly Gly Trp Glu Ile Ile Asp Ile Gly Pro Phe Thr Gln Asn Leu Gly
 1               5                  10                  15

Lys Phe Ala Val Asp Glu Glu Asn Lys Ile Gly Gln Tyr Gly Arg Leu
            20                  25                  30

Thr Phe Asn Lys Val Ile Arg Pro Cys Met Lys Lys Thr Ile Tyr Glu
        35                  40                  45

Asn Glu Gly Ser Arg Glu Ile Lys Gly Tyr Glu Tyr Gln Leu Tyr Val
    50                  55                  60

Tyr Ala Ser Asp Lys Leu Phe Arg Ala Asp Ile Ser Glu Asp Tyr Lys
65                  70                  75                  80

Thr Arg Gly Arg Lys Leu Leu Arg Phe Asn Gly Pro Val Pro Pro Pro
                85                  90                  95

<210> SEQ ID NO 6
<211> LENGTH: 291
<212> TYPE: DNA
<213> ORGANISM: Artificial Sequence
<220> FEATURE:
<223> OTHER INFORMATION: Oligos used for synthesis of the recombinant
      single-chain monellin protein

<400> SEQUENCE: 6
ggtgagtggg agattattga cattggtcca ttcactcaaa acttgggtaa gttcgctgtt      60
gacgaggaga acaagattgg tcaatacggt agattgactt tcaacaaggt tattagacca     120
tgtatgaaga agactattta cgagaacgag ggttctagag agattaaggg ttacgagtac     180
caattgtacg tttacgcttc tgacaagttg ttccgtgctg acatttctga ggactacaag     240
actcgtggtc gtaagttgtt gagattcaac ggtccagttc caccaccata a              291

<210> SEQ ID NO 7
<211> LENGTH: 53
<212> TYPE: DNA
<213> ORGANISM: Artificial Sequence
<220> FEATURE:
<223> OTHER INFORMATION: Oligonucleotide in location M1 in the
      synthesized monellin DNA

<400> SEQUENCE: 7
agaattcggt gagtgggaga ttattgacat tggtccattc actcaaaact tgg             53

<210> SEQ ID NO 8
<211> LENGTH: 55
<212> TYPE: DNA
<213> ORGANISM: Artificial Sequence -continued

```
<220> FEATURE:
<223> OTHER INFORMATION: Oligonucleotide in location M2 in the
      synthesized monellin DNA

<400> SEQUENCE: 8
gaacaagatt ggtcaatacg gtagattgac tttcaacaag tttattaggc catgt          55

<210> SEQ ID NO 9
<211> LENGTH: 59
<212> TYPE: DNA
<213> ORGANISM: Artificial Sequence
<220> FEATURE:
<223> OTHER INFORMATION: Oligonucleotide in location M3 in the
      synthesized monellin DNA

<400> SEQUENCE: 9
gagaccgagg gttctagaga gattaagggt tacgagtacc aattgtacgt ttacgcttc     59

<210> SEQ ID NO 10
<211> LENGTH: 53
<212> TYPE: DNA
<213> ORGANISM: Artificial Sequence
<220> FEATURE:
<223> OTHER INFORMATION: Oligonucleotide in location M4
      in the synthesized monellin DNA

<400> SEQUENCE: 10
gtgctgacat tcctgaggac tacaagactc gtggtcgtaa gttgttgaga ttc           53

<210> SEQ ID NO 11
<211> LENGTH: 59
<212> TYPE: DNA
<213> ORGANISM: Artificial Sequence
<220> FEATURE:
<223> OTHER INFORMATION: Oligonucleotide in location N1 in the
      synthesized monellin DNA

<400> SEQUENCE: 11
gtattgacca atcttgttct cctcgtcaac agcgaactta cccaagtttt gagtgaatg     59

<210> SEQ ID NO 12
<211> LENGTH: 56
<212> TYPE: DNA
<213> ORGANISM: Artificial Sequence
<220> FEATURE:
<223> OTHER INFORMATION: Oligonucleotide in location N2 in the
      synthesized monellin DNA

<400> SEQUENCE: 12
ctctagaacc ctcgttctcg taaatagtct tcttcataca tggtctaata accttg        56

<210> SEQ ID NO 13
<211> LENGTH: 54
<212> TYPE: DNA
<213> ORGANISM: Artificial Sequence
<220> FEATURE:
<223> OTHER INFORMATION: Oligonucleotide in location N3 in the
      synthesized monellin DNA

<400> SEQUENCE: 13
gtcctcagaa atgtcagcac ggaacaactt gtcagaagcg taaacgtaca attg          54

<210> SEQ ID NO 14
<211> LENGTH: 51
<212> TYPE: DNA
<213> ORGANISM: Artificial Sequence
<220> FEATURE:
```

-continued

```
<223> OTHER INFORMATION: Oligonucleotide in location N4 in the
      synthesized monellin DNA

<400> SEQUENCE: 14
agaattctta tggtggtgga actggaccgt tgaatctcaa caacttacga c            51
```